US00PP14735P2

(12) United States Plant Patent
Smith

(10) Patent No.: US PP14,735 P2
(45) Date of Patent: Apr. 27, 2004

(54) CHRYSANTHEMUM PLANT NAMED 'BOLD YOMELISSA'

(50) Latin Name: *Chrysanthemum×morifolium*
Varietal Denomination: Bold Yomelissa

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,529

(22) Filed: Mar. 25, 2003

(51) Int. Cl.[7] ..... A01H 5/00
(52) U.S. Cl. ..... Plt./287
(58) Field of Search ..... Plt./287

*Primary Examiner*—Bruce R. Campell
*Assistant Examiner*—A. Para
(74) *Attorney, Agent, or Firm*—C. A. Whealy

(57) ABSTRACT

A distinct cultivar of Chrysanthemum plant named 'Bold Yomelissa', characterized by its upright, outwardly spreading and mounded plant habit; freely branching habit; uniform and freely flowering habit; decorative-type inflorescences; purple-colored ray florets; and natural season flowering in early October in the Northern Hemisphere.

1 Drawing Sheet

Botanical classification/cultivar designation: *Chrysanthemum×morifolium* cultivar Bold Yomelissa.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Bold Yomelissa'.

The new cultivar is a product of a mutation induction program conducted by the Inventor in Alva, Fla. The objective of the program is to create new garden-type Chrysanthemum cultivars having inflorescences with desirable inflorescence forms, attractive floret colors and good garden performance.

The new Chrysanthemum originated by exposing unrooted cuttings of the Chrysanthemum cultivar Yomelissa, disclosed in U.S. Plant Pat. No. 12,223, to X-ray radiation in June, 1999 in Alva, Fla. Following the radiation treatment, the cuttings were rooted and terminal apices were removed to promote lateral branch development. After lateral branches from the pinch reached sufficient size, terminal cuttings were harvested, planted and flowered in a controlled environment in Alva, Fla. The new Chrysanthemum was discovered and selected by the Inventor as a single flowering plant within this population in November, 1999. The selection of this plant was based on its desirable inflorescence form, attractive ray floret color and good garden performance.

Asexual reproduction of the new cultivar by terminal cuttings taken in a controlled environment in Alva, Fla. since January, 2000, has shown that the unique features of this new Chrysanthemum are stable and reproduced true to type in successive generations.

SUMMARY OF THE INVENTION

The cultivar Bold Yomelissa has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bold Yomelissa'. These characteristics in combination distinguish 'Bold Yomelissa' as a new and distinct cultivar:

1. Upright, outwardly spreading and mounded plant habit.
2. Freely branching habit; dense and full plants.
3. Uniform and freely flowering habit.
4. Decorative-type inflorescences.
5. Purple-colored ray florets.
6. Natural season flowering in early October in the Northern Hemisphere.

Plants of the new Chrysanthemum are most similar to plants of the the cultivar Yomelissa. In side-by-side comparisons conducted in Alva, Fla., plants of the new Chrysanthemum differed from plants of the cultivar Yomelissa in the following characteristics:

1. Plants of the new Chrysanthemum flowered about two to three days later than plants of the cultivar Yomelissa.
2. Ray florets of the new Chrysanthemum were darker purple in color than ray florets of the cultivar Yomelissa.

Plants of the new Chrysanthemum can also be compared to plants of the Chrysanthemum cultivar Heather, disclosed in U.S. Plant Pat. No. 9,440. In side-by-side comparisons conducted in Alva, Fla., plants of the new Chrysanthemum differed from plants of the cultivar Heather in the following characteristics:

1. Plants of the new Chrysanthemum were shorter than plants of the cultivar Heather.
2. Plants of the new Chrysanthemum flowered about five days earlier than plants of the cultivar Heather.
3. Plants of the new Chrysanthemum had larger inflorescences than plants of the cultivar Heather.
4. Ray floret color of plants of the new Chrysanthemum did not fade as readily as ray floret color of plants of the cultivar Heather.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Bold Yomelissa'.

The photograph at the bottom of the sheet comprises a close-up view of typical inflorescences of the cultivar 'Bold Yomelissa'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Salinas, Calif., under natural season conditions and practices which approximate those generally used in commercial garden-type Chrysanthemum production. One cutting was planted in a 15.25-cm container in late May, 2002. Plants were not pinched, that is, the terminal apex was not removed to enhance branching. During the production of the plants, day temperatures averaged 20° C. and night averaged 13° C. Measurements and numerical values represent averages for typical flowering plants.

Botanical classification: *Chrysanthemum×morifolium* cultivar Bold Yomelissa.

Commercial classification: Decorative-type garden Chrysanthemum.

Parentage: Induced mutation of the *Chrysanthemum×morifolium* cultivar Yomelissa, disclosed in U.S. Plant Pat. No. 12,223.

Propagation:

*Type.*—Terminal tip cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Appearance.*—Perennial herbaceous decorative-type garden Chrysanthemum. Inverted triangle with rounded crown. Stems initially upright, then somewhat outwardly spreading giving a uniformly mounded appearance to the plant. Freely branching with lateral branches forming at every node.

*Plant height.*—About 23 cm.

*Plant diameter.*—About 32 cm.

*Lateral branches.*—Length: About 20 cm. Diameter: About 5 mm. Internode length: About 1.5 cm. Aspect: Upright and outwardly spreading. Texture: Pubescent. Color: 146A faintly overlain with 187A.

*Foliage description.*—Leaf arrangement: Alternate. Length: About 5.3 cm. Width: About 4.4 cm. Apex: Cuspidate. Base: Truncate. Margin: Palmately lobed, sinuses parallel to divergent. Texture, upper surface: Slightly pubescent. Texture, lower surface: Pubescent; veins prominent. Color: Developing and fully expanded foliage, upper surface: 147A. Developing and fully expanded foliage, lower surface: 147B. Venation, upper surface: 147A to 147B. Venation, lower surface: 147B. Petiole length: About 1.2 cm. Petiole diameter: About 2 mm. Petiole color, upper surface: Close to 147B to 147C. Petiole color, lower surface: Close to 147B.

Inflorescence description:

*Appearance.*—Decorative-type inflorescence form with elongated oblong-shaped ray florets. Inflorescences borne on terminals above foliage, arising from leaf axils. Disk and ray florets developing acropetally on a capitulum. About seven inflorescences per lateral.

*Flowering response.*—Under natural season conditions, plants flower in early October in the Northern Hemisphere.

*Inflorescence bud (before showing color).*—Height: About 4.5 mm. Diameter: About 7 mm. Shape: Oblate. Color (lower surface of phyllaries): Close to 147A.

*Inflorescence size.*—Diameter: About 5.5 cm. Depth (height): About 2.2 cm. Disc diameter: No disc florets observed. Receptacle diameter: About 5.5 mm.

*Ray florets.*—Shape: Elongated oblong. Length: About 2.7 cm. Corolla tube length: About 4 mm. Width: About 7 mm. Apex: Mostly emarginate. Margin: Entire. Texture: Smooth, glabrous; satiny. Surface: Concave to mostly flat. Orientation: Initially upright, then perpendicular to vertical. Number of ray florets per inflorescence: About 169 in numerous whorls. Color: When opening, upper surface: Initially close to 155D; color becoming close to 155D overlain with darker than 77A. When opening, lower surface: Initially close to 155D; color becoming close to 155D underlain with darker than 77A. Opened inflorescence, upper surface: Close to 77A; color becoming lighter than 77A with development. Opened inflorescence, lower surface: Close to 155D underlain with 77A.

*Disc florets.*—No disc florets observed.

*Peduncle.*—Strength: Strong. Aspect: About 45 to 50° from vertical. Length: First peduncle: About 5.7 cm. Fourth peduncle: About 9.2 cm. Seventh peduncle: About 10.5 cm. Diameter: About 3 mm. Texture: Pubescent. Color: 146A faintly overlain with 187A.

*Phyllaries.*—Quantity per inflorescence: About 30. Length: About 7 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Reproductive organs.*—Androecium: Not observed. Gynoecium: Present on ray florets.

*Seed/fruit.*—Seed and fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 37° C.

It is claimed:

1. A new and distinct cultivar of Chrysanthemum plant named 'Bold Yomelissa', as illustrated and described.

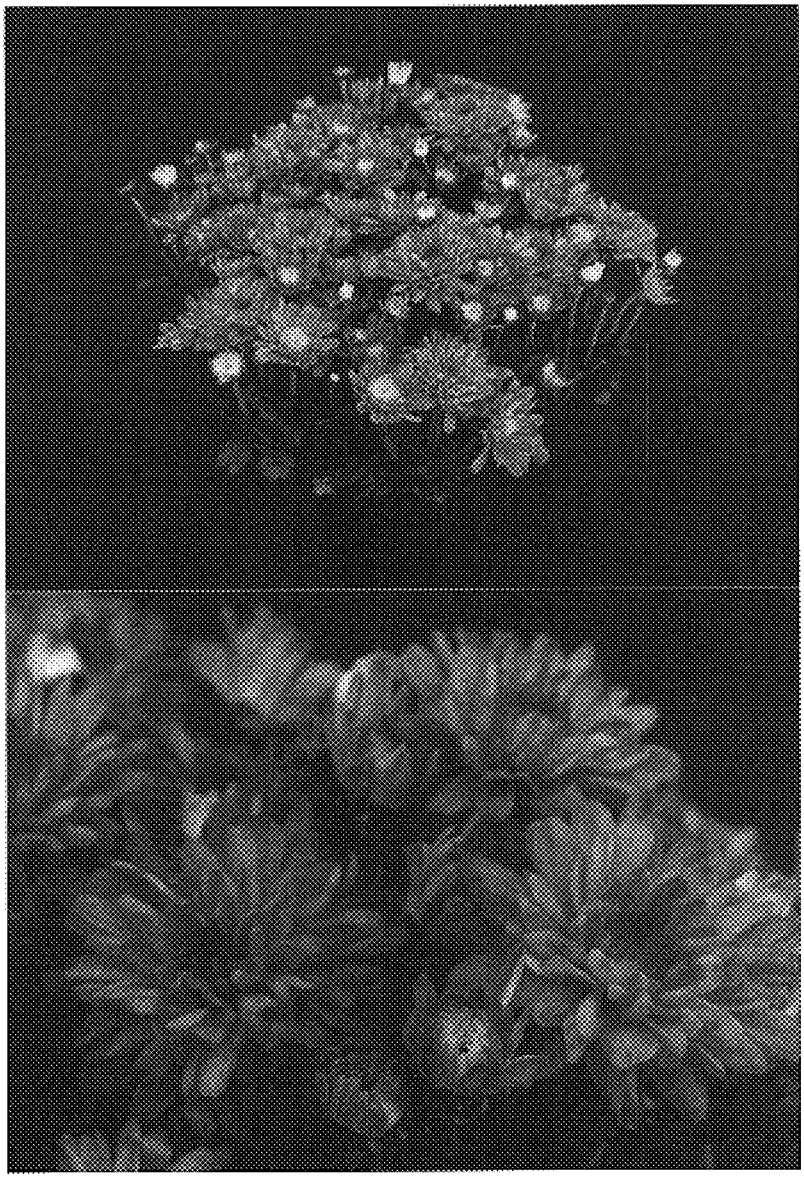

* * * * *